United States Patent [19]

Silver

[11] Patent Number: 4,728,195

[45] Date of Patent: Mar. 1, 1988

[54] METHOD FOR IMAGING PRINTED CIRCUIT BOARD COMPONENT LEADS

[75] Inventor: William M. Silver, Medfield, Mass.

[73] Assignee: Cognex Corporation, Needham, Mass.

[21] Appl. No.: 841,287

[22] Filed: Mar. 19, 1986

[51] Int. Cl.[4] ............................................. G01B 11/00
[52] U.S. Cl. .................................... 356/394; 356/237; 356/398
[58] Field of Search ................. 29/720, 721, 832, 833, 29/840; 356/394, 237, 398

[56] References Cited

U.S. PATENT DOCUMENTS 4,240,750 12/1980 Kurtz et al. .

FOREIGN PATENT DOCUMENTS 107202 6/1984 Japan ..................................... 29/833

Primary Examiner—Timothy V. Eley
Attorney, Agent, or Firm—Lahive & Cockfield

[57] ABSTRACT

The invention provides a novel system for imaging a component lead on an assembled printed circuit board. The system incorporates a light source for illuminating a substantial portion of a solder pad of the circuit board being inspected. A photoreceptor receives emissions reflected from the illuminated portion of said solder pad and generates an image representative thereof. This photoreceptor is arranged so that passage of a component lead through the component hole occludes or shadows a portion of the solder pad from which the photoreceptor would otherwise receive reflected emissions. The system has application in the testing of printed circuit boards prior to wave soldering.

5 Claims, 9 Drawing Figure

METHOD FOR IMAGING PRINTED CIRCUIT BOARD COMPONENT LEADS

BACKGROUND

The invention relates to the inspection of printed circuit boards and, more particularly, to methods and apparatus for imaging component leads in assembled printed circuit boards. The invention has application in the testing of printed circuit boards prior to wave soldering.

To reduce production costs, and to improve quality and reliability, a printed circuit board is checked at many stages throughout its manufacture. One critical testing stage, for example, is in the period following assembly of electrical components on the board and prior to soldering of the components' leads. Detection of faults at this stage facilitates the inexpensive repair of assembly defects, which may be impossible to detect after soldering.

In the pre-solder stage, the assembled boards are difficult to inspect. They cannot be inspected electrically because reliable connections are not yet established. The testing method of choice therefore is visual inspection, preferably by machine. This inspection is intended to reveal faulty component lead placement, including improper lead bending, which may prevent a component lead from passing through a component hole, and improper lead direction, which may result in a lead contacting a neighboring solder pad.

Visual inspection of printed circuit boards by machine requires the use of a device for producing images representative of component lead placement. Among the prior art methods for producing such images is the so-called "bright leads technique." According to this process, an assembled board is illuminated from the side. A camera is placed above the board and, specifically, above a component hole to be inspected. If a component lead has been properly inserted through the hole, light from the illuminating source reflects off the lead and toward the camera. This reflection appears as a bright spot centered about the component hole. In the event a component lead has not been properly inserted, no bright spot appears at the camera.

One drawback of the bright leads technique is that it does not consistently produce a bright spot, even when the component lead is properly positioned. This defect arises, in part, because component leads are highly specular surfaces, i.e., they reflect incident light in a very small cone. If a properly placed lead is not oriented in the expected direction, reflection from the lead will not reach the inspection camera lens. Consequently, a bright spot will not appear in the image, and a defect will be indicated where none actually exists.

The art provides other imaging devices employing variations on the basic bright leads technique which are intended to reduce problems caused by lead misorientation. These devices use multiple cameras to catch light reflected in a number of directions. Although this technique increases the likelihood that at least one camera will see the lead, it still provides no guarantee that a properly placed lead will actually be detected. Moreover, the use of multiple cameras increases both the cost of the testing equipment and the time required to examine the images produced by those cameras.

Kurtz et al, U.S. Pat. No. 4,240,750, discloses another prior art technique for imaging component lead placement. According to this publication, a laser beam is scanned, for example, on a degree-by-degree basis around the solder pad of a printed circuit component hole. Presence of a lead on the solder pad is signified by differing beam reflectance at the spot where the lead crosses the solder pad. One drawback of the Kurtz et al technique is the expense required to practice it. Another is the enormous amount of time required to inspect each solder pad while the laser beam makes its step-by-step procession around the pad parameter.

An object of this invention is to provide improved imaging equipment for use in the inspection of assembled printed circuit boards. More particularly, an object is to provide an improved method and apparatus for generating images of component lead placement in circuit board component holes.

Another object of the invention is to provide a system for printed circuit board component lead imaging which utilizes relatively inexpensive equipment.

Still another object of the invention is to provide a reliable system for printed circuit board component lead imaging which produces images incorporating necessary information to facilitate interpretation of lead placement.

Yet another object of the invention is to provide a system for printed circuit board component lead imaging which may be readily adapted to pre-existing assembly line equipment.

Still further objects of the invention are evident in the drawings and description which follows.

SUMMARY OF THE INVENTION

The invention is based, in part, upon a novel use of printed circuit board solder pads for component lead imaging. Unlike component leads themselves, printed circuit board solder pads have highly specular surfaces of well constrained orientation. These pads reflect light in such a way as to provide highly consistent reflectance patterns. By utilizing these reflectance patterns and, particularly, changes resulting from shadowing or occlusion, the presence of component leads may be readily determined.

One aspect of the invention therefore provides a novel method for imaging a component lead on an assembled printed circuit board. The method calls for illuminating with a light source a substantial portion of a solder pad being inspected. A photoreceptor receives emissions reflected from the illuminated portion of said solder pad and generates an image representative thereof. This photoreceptor is arranged so that passage of the component lead through the component hole occludes or shadows a portion of the solder pad from which the photoreceptor would otherwise receive reflected emissions.

In another aspect, the invention provides a method for component lead imaging including the step of arranging the light source to provide emissions having a non-zero angle of incidence with respect to the solder pad. Similarly, the photoreceptor is arranged to receive emissions having a non-zero angle of reflectance with respect to the solder pad. According to this aspect of the invention, the angle of incidence and the angle of reflectance can be equal. As used hereinafter, a non-zero angle of incidence or reflectance occurs so long as the angle of incident light and the angle of reflected light are not both directly perpendicular to a reflecting plane of the solder pad; that is, so long as the light source and photoreceptor are not arranged for so-called "normal" reflectance.

According to another aspect of the invention, the light source and the photoreceptor are arranged to at respective angles of incidence and reflectance between 30 and 60 degrees. In yet another aspect, these angles are set to 45 degrees.

Still other aspects of the invention relate to an apparatus operating according to the method described above.

DETAILED DESCRIPTION OF THE ILLUSTRATED EMBODIMENT

Figure 1A:
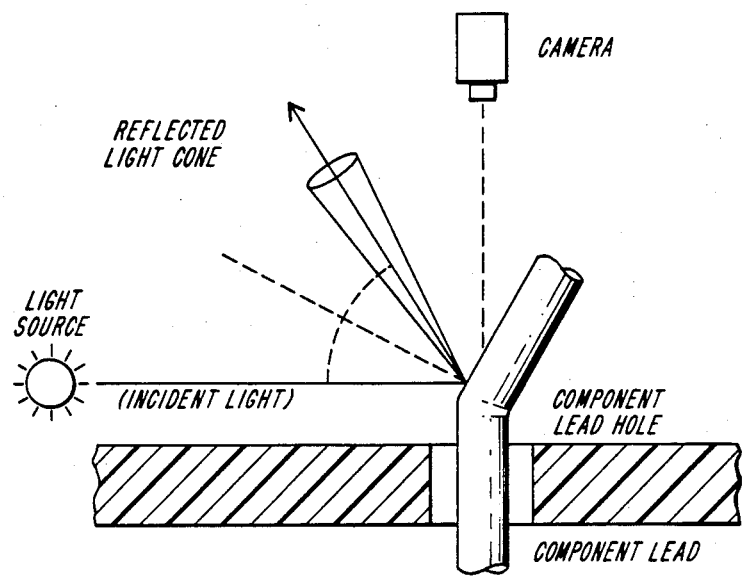
FIG. 1(a), 1(b), and 1(c) depict a practice of the prior art bright leads technique and component lead images produced thereby.

FIG. 1a depicts a practice of component lead imaging according to the prior art bright leads technique. According to the illustrated practice, a light source illuminates an assembled circuit board from the side. A component lead inserted through a component hole of the board reflects incident light in a cone centered about a reflectance angle equal to the angle of incidence. An imaging camera positioned directly above the component hole is intended to receive light reflected from the component lead.

Figure 1B:
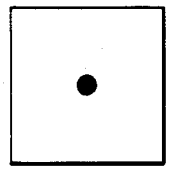
Figure 1C:
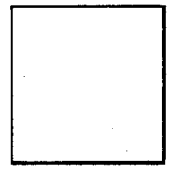

However, as shown in the illustration, due to the peculiar orientation of the component lead, the cone of light reflected from the lead is not received at the camera. While reflectance from the lead is normally expected to produce a so-called "bright lead" image, depicted in FIG. 1b, misorientation of the lead's reflecting surface results in a "no lead" image at the camera. This image, which does not contain a bright spot at the center of the component hole, is depicted in FIG. 1c.

Figure 2:
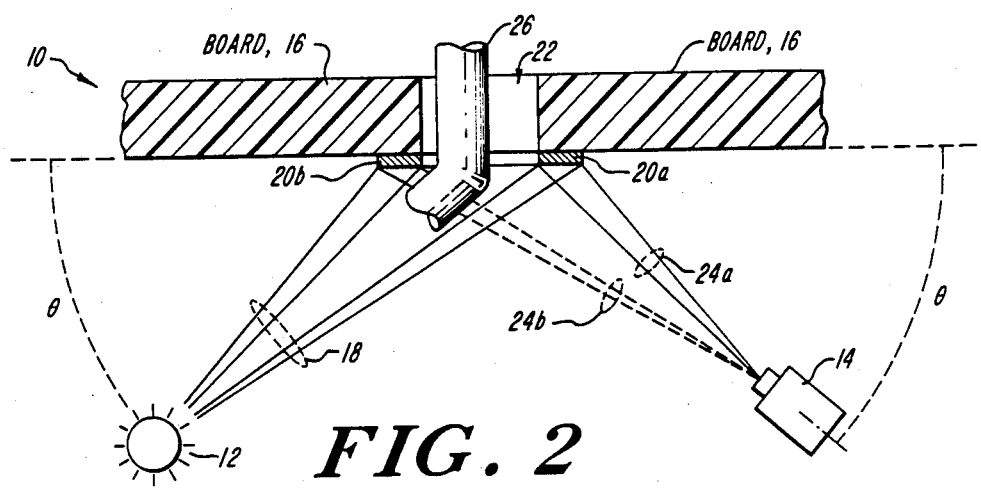
FIG. 2 illustrates an embodiment of an imaging apparatus constructed in accord with one practice of the invention.

FIG. 2 illustrates a novel apparatus for component lead imaging constructed in accord with one practice of the invention. The illustrated apparatus 10 includes a light source 12 and a photoreceptor 14, both arranged at an elevation angle ($\theta$) with respect to the component board 16 surface. Incident light beams 18 generated by the light source 12 simultaneously illuminate at least a substantial portion of a solder pad, having portions 20a and 20b, disposed about component hole 22 on the backplane of the board 16.

As further shown in FIG. 2, light reflecting off the solder pad is directed to the photoreceptor 14. More particularly, light reflected off solder pad portion 20a travels along pathway 24a to the lens of the photoreceptor 14. Component lead 26, however, blocks light reflected off pad 20b from reaching the photoreceptor 14. Dashed lines 24b indicate the pathway the blocked light would have taken in the absence of occlusion by the component lead 26.

According to a preferred practice, the light source 12 can be arranged to provide emissions having an angle of incidence between 30 and 60 degrees and, preferably, 45 degrees with respect to the backplane of the circuit board 16 and, more particularly, to the reflecting surface of the solder pad. The photoreceptor can be similarly arranged to receive emissions reflected off the solder pad at an angle between 30 and 60 degrees, preferably, 45 degrees with respect to the solder pad reflecting surfaces. These preferred angles represent a compromise between shallow angles, which give rise to oblong reflection patterns that are difficult to interpret, and steep angles, which give rise to short component lead signatures that are difficult to detect.

According to a preferred practice of the invention, the light source 12 is slightly extended. This is preferable since the solder pads are typically not perfectly flat and since the angle of reflectance can vary slightly, e.g., up to two degrees, over the field of view of the photoreceptor. One preferred illumination source is a 60 watt incandescent bulb mounted in a 5-inch diameter white reflector, resulting in a light source having an extent of 5 inches.

A preferred photoreceptor is solid state black and white television camera with a rectangular array of CCD sensors producing a standard RS-170 video signal. A camera of this type produces geometrically accurate images representative of the reflectance pattern of the solder pad and board, which images are readily adapted to interface to commercially available machine vision equipment.

Each sensing element of the camera 14 generates a single measurement of scene brightness at a corresponding portion of the circuit board or solder pad. These elements are referred to as pixels. A preferred resolution for the illustrated imaging system is 0.002 inches/pixel, as measured on the board rather than at the camera. It will be appreciated that this resolution represents a trade-off between information content and time required to inspect the resultant image. While a preferred resolution is 0.002 inches/pixel, resolutions between 0.0001 inches/pixel and 0.004 inches/pixel also produce acceptable results.

A total field of view provided by camera 14 arranged with the preferred resolution is approximately 1 square inch. This area is typically not large enough to view an entire printed circuit. Accordingly, a mechanical device, e.g., a linear actuator, can be used to position either the board or the camera 14 and the light source 12 to permit inspection of the entire board.

An aperture setting for the camera 14 arranged in the illustrated set-up is determined by the amount of light available, the sensitivity of the camera and the exposure time. For example, using a preferred RS-170 video camera, with a 1/30 second exposure time, and a 60 watt bulb, an aperture as small as f/11 to f/13 can be used. This small aperture provides excellent depth of field, which is important when viewing the scene at a 45 degree elevation.

As discussed in greater detail below, the reflectance pattern from the solder pads is distorted for angles of elevation other than 90 degrees, i.e., non-zero reflectance angles. The degree of distortion depends upon the the distance between the photoreceptor and the solder pad, as well as the size of the field of view of the camera. If the camera-subject distance is large, as compared with the size of the field of view, the perspective distortion approaches zero and the transformation from image coordinates to circuit board coordinates may be accomplished according to well known techniques by a simple 2×2 rotation/scale/skew matrix.

A preferred distance of twenty-four inches between the photoreceptor and the solder pads, however, is sufficiently distant, when compared with a 1 square-inch field of view to make the perspective distortion insignificant. It will be appreciated that this distance is not so great as to require the use of long focal length lenses, which are large, expensive and heavy. For the illustrated embodiment, a preferred focal length is 135 mm.

Figure 3A:
FIG. 3(a), 3(b), and 3(c) illustrate component lead signatures produced by an apparatus operating in accord with one practice of the invention.
Figure 3B:
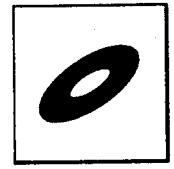

The apparatus 10 produces component lead and reflectance images of the type shown in FIGS. 3a, 3b, 3c, 3d, and 3e. In particular, FIG. 3a shows the reflectance pattern received from a square solder pad in the absence of a component lead passing through the corresponding component hole. The reflectance pattern from the square pad appears as a rhombus as a result of the angular elevation of the photoreceptor. FIG. 3b shows a reflectance pattern received from a circular solder pad in the absence of a component lead. The reflectance pattern from the circular pad appears as an oval, also as a consequence of the elevation of the photoreceptor. It will be appreciated that the apparatus 10 can produce reflectance images not only for square and circular solder pads, but also for pads of any other geometrical configuration.

Figure 3C:
Figure 3D:
Figure 3E:
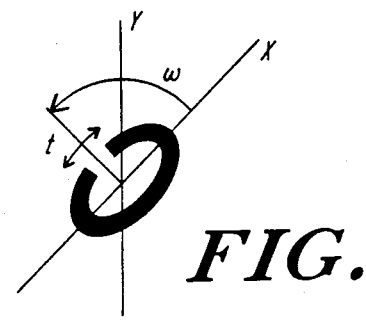

FIGS. 3c and 3d show component lead signatures produced by apparatus 10 in the presence of component leads in the component holes. As discussed in greater detail below, the protrusion of the component lead into the backplane space of the circuit board causes shadowing of the solder pad or occlusion of the reflected light. This shadowing or occlusion effectively blocks the pad's reflectance pattern at the photoreceptor, thus, producing a break in the image. This break may extend radially through the entire reflectance pattern, as shown in FIGS. 3c–3e, or it may extend only partially into such pattern More particularly, FIG. 3c illustrates the reflectance pattern received from a square solder pad where the protruding lead shadows or occludes a portion of the reflected light. FIG. 3d similarly illustrates the effect of a protruding lead shadowing or occluding a circular pad.

FIG. 3e illustrates details of a component lead signature similar to that shown in FIG. 3c. The illustrated coordinate system corresponds to a projection of an orthogonal coordinate system on the backplane of the circuit board. The illustrated coordinate system is skewed as a result of the positioning of the photoreceptor.

In FIG. 3e, the angle (w) represents the projected component lead wipe angle, as received at the photoreceptor. This angle (w) can be measured by image analysis equipment (not illustrated) from the x-axis of the coordinate system. The actual wipe angle of the component lead can be calculated from this angle (w) and the component lead clinch angle. FIG. 3e also illustrates a lead thickness angle (t), which can be analyzed to determine whether the break in the reflectance pattern truly represents a component lead.

Figure 4:
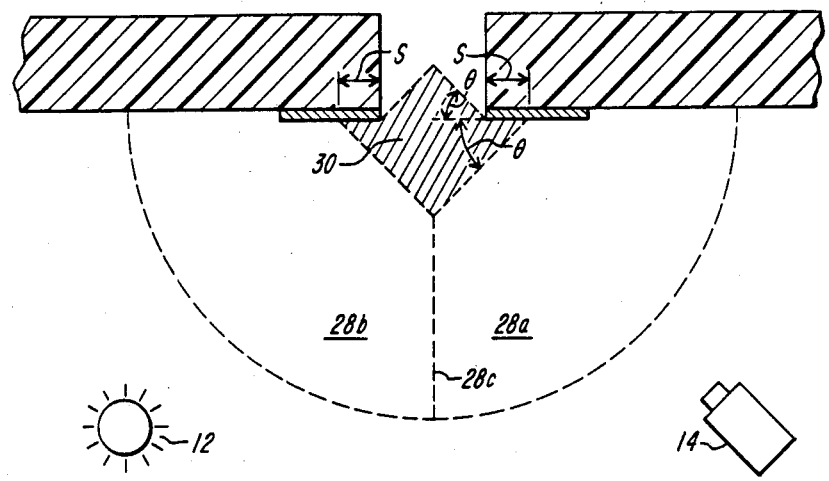
FIG. 4 illustrates a geometry by which component lead signatures are produced in an apparatus constructed according to one practice of the invention.

FIG. 4 illustrates the geometry which underlies the production of component lead signatures in an imaging apparatus constructed in accord with the invention. According to this geometry, where a component lead enters a hemisphere 28a on the photoreceptor 14 side of the component hole, the lead casts a shadow on the solder pad. Where, on the other hand, the lead penetrates a hemisphere 28b on the light source 12 side of the component hole, the lead occludes the photoreceptor's view of the bright pad. Moreover, where the component lead is near the boundary of the two hemispheres, indicated by dashed line 28c, both shadowing and occlusion can occur. This, in turn, gives rise to a double signature, i.e., two breaks in the reflectance pattern from the solder pad.

Regardless of which hemisphere 28a or 28b the component lead penetrates, the lead image will appear in sharp contrast to the illuminated pad. This occurs because the pad, which is bathed in light, provides specular reflectance over its entire surface. The component lead, on the other hand, is not oriented for specular reflection in the direction of the photoreceptor. Thus, less light is reflected from the lead to the photoreceptor.

According to this arrangement, it is seen that specular surfaces which are not perfectly aligned with the solder pads will reflect only insignificant amounts of light, if any, to the photoreceptor. Thus, the imaging apparatus serves as a filter, reflectively passing emissions only from those surface elements which are parallel to the circuit board, while effectively blocking emissions from those surface elements having any other orientation.

With continued reference to FIG. 4, component leads which do not enter either of hemispheres 28a or 28b, but, instead, remain in shaded region 30, may or may not produce component lead signatures.

Figure 5:
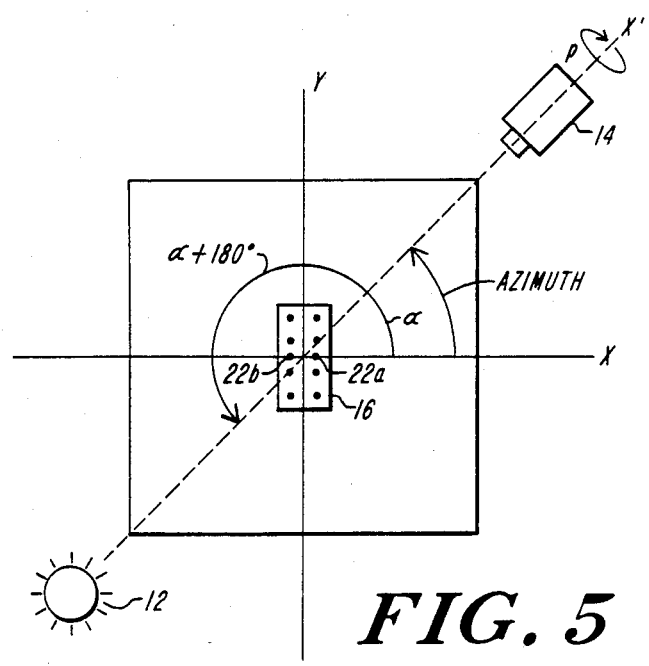
FIGS. 5 illustrates an enhanced arrangement of elements in the apparatus depicted in FIG. 2.

FIG. 5 presents further improvements on the apparatus 10 (FIG. 2) for enhancing component lead signature detection. According to the practice illustrated in FIG. 5, the light source 12 and the photoreceptor 14 are aligned on an axis, x', which lies on the α-azimuth of the circuit board 16. This azimuth corresponds to the rotation of the board's x-axis, defined, e.g., by component holes 22a and 22b, as illustrated. The illustrated arrangement reduces the tendency of the component leads to shadow or occlude neighboring solder pads. A preferred angle of the azimuth rotation, α, is between 40 and 50 degrees and, preferably, is 45 degrees.

When arranging the light source 12 and photoreceptor 14 along the α-azimuth, components with many leads, such as dips, may not fit in one field of view. The illustrated apparatus partially compensates for this by rolling, by ρ degrees, the photoreceptor 14. A preferred roll angle, ρ, is between 40 and 50 degrees and, preferably, is 45 degrees.

In accordance with the above description, the invention attains the objects set forth. The invention provides an improved system for printed circuit board component lead imaging. This system produces consistent component lead signatures which incorporate necessary information to facilitate interpretation of lead placement. The system is also adapted for retrofit to existing circuit board assembly line equipment.

It is intended that all matter in the description and drawings be interpreted as illustrative and not in a limiting sense. Those skilled in the art may have changes described in the embodiment, and in other teachings herein, for further practices which are within the scope of the invention described and claimed herein.

What is claimed is:

1. A method for generating a component pin signature for an assembled printed circuit board, the method comprising the steps of (A) simultaneously illuminating with a light source at least a substantial portion of a solder pad of the circuit board, said solder pad being associated with a component hole in the board and being arranged for electrical connection with a component lead passed through the component hole, (B) receiving with a photoreceptor emissions reflected from the illuminated portion of said solder pad, said photoreceptor being so arranged that passage of the component lead through the component hole occludes or shadows a portion of the solder pad from which the photoreceptor would otherwise receive reflected emissions, and (C) generating an imaging signal representative of emissions received at the photoreceptor.

2. A method according to claim 1, wherein step (A) includes the step of arranging the light source for providing emissions having designated angle of incidence to a reflecting surface of the solder pad, and step (B) includes the step of receiving emissions reflected from the solder pad at a designated angle of reflectance to the reflecting surface of the solder pad, the angle of incidence and the angle of reflectance being substantially equal and substantially non-zero.

3. A method according to claim 1, wherein step (A) includes the step of arranging the light source for providing emissions having a designated angle of incidence to a reflecting surface of the solder pad, and step (B) includes the step of receiving emissions reflected from the solder pad at a designated angle of reflectance to the reflecting surface of the solder pad, each of said designated angle of incidence and said designated angle of reflectance being in the range of 30 to 60 degrees.

4. A method according to claim 1, wherein step (A) includes the step of arranging the light source for providing emissions having a designated angle of incidence to a reflecting surface of the solder pad, and step (B) includes the step of receiving emissions reflected from the solder pad at a designated angle of reflectance to the reflecting surface of the solder pad, each of said designated angle of incidence and said designated angle of reflectance being substantially equal to 45 degrees.

5. A method according to claim 1, wherein step (A) includes the step of providing within the light source a diffuser element for diffusing emissions which are to illuminate the solder pad.

* * * * *